(12) United States Patent
Fenlon

(10) Patent No.: US 10,086,155 B2
(45) Date of Patent: Oct. 2, 2018

(54) METERED-DOSE INHALER

(71) Applicant: IVAX PHARMACEUTICALS IRELAND, Utrecht (NL)

(72) Inventor: Derek Fenlon, Waterford (IE)

(73) Assignee: Ivax Pharmaceuticals Ireland, Waterford (IE)

( * ) Notice: Subject to any disclaimer, the term of this patent is extended or adjusted under 35 U.S.C. 154(b) by 843 days.

(21) Appl. No.: 14/148,943

(22) Filed: Jan. 7, 2014

(65) Prior Publication Data

US 2014/0116428 A1    May 1, 2014

Related U.S. Application Data

(62) Division of application No. 12/528,740, filed as application No. PCT/EP2008/001514 on Feb. 26, 2008.

(60) Provisional application No. 60/903,590, filed on Feb. 27, 2007.

(51) Int. Cl.
*A61M 15/00* (2006.01)

(52) U.S. Cl.
CPC ...... *A61M 15/0065* (2013.01); *A61M 15/009* (2013.01); *A61M 15/0071* (2014.02); *A61M 2205/6063* (2013.01); *A61M 2205/6081* (2013.01); *Y10T 29/49826* (2015.01)

(58) Field of Classification Search
CPC .......... A61M 15/0065; A61M 15/0071; A61M 15/0078; A61M 15/009; A61M 2205/6063; A61M 2205/6081; A61M 11/00; A61M 15/00; A61M 15/0001; A61M 15/0028; A61M 15/003; A61M 2205/12; A61M 2205/123

USPC ........... 128/200.14, 200.23, 205.23; 40/310, 40/311, 661.09; 116/308, 309

See application file for complete search history.

(56) References Cited

U.S. PATENT DOCUMENTS

2002/0162261 A1    11/2002   West et al.
2003/0230304 A1    12/2003   Blacker et al.
(Continued)

FOREIGN PATENT DOCUMENTS

EP    966309    7/1998
FR    0453057   6/2006
(Continued)

OTHER PUBLICATIONS

International Search Report, dated Jun. 9, 2008, corresponding to International Application No. PCT/EP2008/001514.

*Primary Examiner* — Jackie Tan-Uyen T Ho
*Assistant Examiner* — Joseph D Boecker
(74) *Attorney, Agent, or Firm* — Morgan, Lewis & Bockius, LLP

(57) ABSTRACT

An inhaler including a medicament-containing vessel; an actuator body for receiving the vessel and having a medicament delivery outlet, wherein the vessel is releasably attachable to the actuator body; a dose counter integrated into the actuator body; and a first indicium on the vessel and a second indicium on the actuator body, wherein the first indicium and the second indicium identify the vessel and the actuator body to be part of the same metered-dose inhaler. Also provided is a kit including the metered-dose inhaler and at least one pair of stickers and a method for manufacturing the metered-dose inhaler.

11 Claims, 1 Drawing Sheet

(56) References Cited

U.S. PATENT DOCUMENTS

Figure 1:
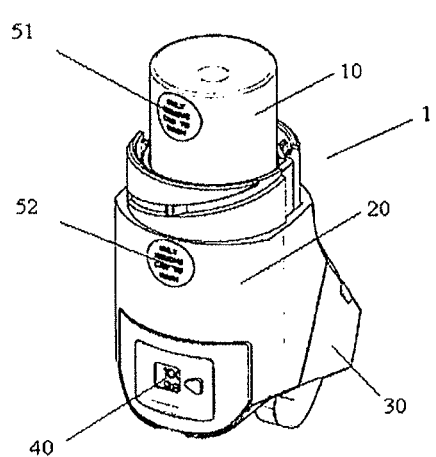

| | | | |
|---|---|---|---|
| 2004/0060212 A1* | 4/2004 | Murphy | G09F 3/00 |
| | | | 40/324 |
| 2005/0081846 A1* | 4/2005 | Barney | A61M 15/0065 |
| | | | 128/200.23 |
| 2005/0133155 A1 | 6/2005 | Leder et al. | |
| 2005/0218026 A1* | 10/2005 | Gold | B65D 17/165 |
| | | | 206/459.1 |
| 2006/0175345 A1* | 8/2006 | Lu | A61M 15/009 |
| | | | 222/23 |
| 2008/0010874 A1* | 1/2008 | Londino | A61J 7/04 |
| | | | 40/310 |
| 2008/0017188 A1* | 1/2008 | Pardonge | A61M 15/009 |
| | | | 128/200.14 |
| 2008/0098630 A1* | 5/2008 | Frankenbach | G09F 23/00 |
| | | | 40/312 |
| 2009/0165788 A1* | 7/2009 | Warden | A61M 15/0028 |
| | | | 128/203.15 |

FOREIGN PATENT DOCUMENTS

| | | |
|---|---|---|
| WO | WO 98/28033 | 7/1998 |
| WO | WO 01/08733 A1 | 2/2001 |
| WO | WO 2006/064159 A1 | 6/2006 |

* cited by examiner

METERED-DOSE INHALER

CROSS-REFERENCE TO RELATED APPLICATIONS

This application is a divisional patent application of U.S. Non-Provisional patent application Ser. No. 12/528,740, filed Aug. 26, 2009, which claims priority to International Patent Application No. PCT/EP2008/001514, filed Feb. 26, 2008, which claims priority to U.S. Provisional Patent Application No. 60/903,590, filed Feb. 27, 2007, all of which are incorporated by reference herein in their entirety.

BACKGROUND OF THE INVENTION

This invention provides a metered-dose inhaler comprising a medicament-containing vessel, an actuator body for releasably attaching the vessel to the body and having a medicament delivery outlet, a dose counter integrated into the actuator body; and indicia on the vessel and the actuator body, said indicia identifying the vessel and the actuator body to be part of the same metered-dose inhaler. Also provided is a kit comprising the medicament-containing vessel, the actuator body, the dose counter and at least one pair of stickers releasably attached to a backing sheet and comprising a first sticker and the second sticker which can be identified as being part of the pair. The invention further provides a method for manufacturing the metered-dose inhaler comprising the steps of providing the medicament-containing vessel, providing the actuator body, releasably attaching the vessel to the actuator body, and subsequently attaching a first indicium to the vessel and a second indicium to the actuator body, such that the first indicium and the second indicium identify the vessel and the actuator body to be part of the same metered-dose inhaler.

Commonly the contents of the medicament-containing vessel are not visible by the user, for example, when the inhaler is a pressurised metered-dose inhaler (of both manually-operable and breath-actuated types) or dry-powder inhalers.

One of the drawbacks of self-administration using an inhaler is that users often experience difficulty in determining when the medicament in the medicament-containing vessel (canister) is nearly exhausted. With aerosol canisters, part of the reason for this difficulty is that a surplus of propellant may remain in the canister even though the medicament supply is nearly used up. This leads the user to believe that the inhaler is still capable of providing useful doses of medicament simply because the canister contains liquid. Alternatively, the near-exhausted state may result in a surplus of medicament in relation to propellant.

The prospect of the medicament unexpectedly running out is potentially hazardous for the user because the delivered dose becomes variable towards the end of the dosing regime. Likewise few users routinely carry a second back-up inhaler on them.

One strategy used by users is to have several different inhalers that are kept at a different locations, such as at school, home, work etc. In these circumstances it is particularly difficult for the user to keep track of the amount of usage extracted from each individual inhaler.

Clearly there is a need for a counter mechanism which enables users to assess how many doses remain in the obscured vessel. Such a counter would ensure that users are warned when the inhaler nears exhaustion so that appropriate measures can be taken to avoid running out of medication.

Recognising this risk, in March 2003 the US Food and Drug Administration issued a Guidance for Industry document (Integration of Dose-Counting Mechanisms for Metered-Dose Inhaler Medicament Products), which set out the requirement that all new metered-dose inhalers are required to have a dose counter in order to allow the patient to see how many doses remain in the inhaler. This requirement relates to all new inhalers for the US market, and hence is an important consideration for all manufacturers.

Several methods for counting the remaining doses in metered-dose inhalers have been disclosed. EP 0 966 309, which is incorporated by reference, discloses a mechanical dose counter in which administration of a dose of medicament by the inhaler causes a visible display indicating the number of medicament doses remaining in the inhaler to decrease by one.

Specifically, EP 0 966 309 discloses a dose counter comprising actuator means; drive means for driving rotary gear means in step-wise fashion in response to displacement of said actuator means, said rotary gear means comprising a wheel mounted on a spindle and said wheel having a plurality of ratchet teeth around its periphery; means to prevent reverse rotation of said rotary gear means; display means coupled to the rotary motion of said rotary gear means, said display means having a visible array of incrementing integers on a surface thereof indexable by a single integer in response to each step of the step-wise rotary motion of the rotary gear means; and said dose counter further comprises a control surface to regulate the position of engagement and disengagement between said drive means and said wheel.

In the case of the dose counter described above, as is common in metered-dose inhalers, the dose counter is integrated into the actuator body of the metered-dose inhaler rather than the medicament-containing vessel. Further, the actuator body and the medicament-containing vessel of metered-dose inhalers are generally separable from each other.

Consequently, there is a risk that after separation of the actuator body and the medicament-containing vessel (for example when washing the actuator if it becomes clogged), the actuator body may be mismatched with a different medicament-containing vessel to the one to which it was previously attached. After mismatching, the dose counter would clearly not then accurately reflect the remaining number of doses in the medicament-containing vessel.

It is worthy of note that users often have multiple metered-dose inhalers, and therefore the risk of mismatching can be significant. Further, the consequences of a dose counter inaccurately reflecting the number of doses in the medicament-containing vessel could be severe, as this could result in a patient being without medication when needed. There is therefore a need in the art for a solution to this potentially hazardous problem.

WO2006/064159 A1, which is incorporated by reference, discloses a fluid dispenser device comprising: a reservoir of fluid to be disposed; a dispenser member, such as a pump or a valve, mounted on said reservoir; and a body that is suitable for receiving said reservoir, said body being provided with a dispenser orifice and an opening through which said reservoir can be inserted into the body, said reservoir can be inserted into the body between a rest position and a dispensing position, said reservoir being removable from said body; the device being characterised in that said reservoir and said body include respective ID means that make it possible to associate said reservoir with said body.

There is a need for improved solution to the problem of mismatching medicament-containing vessels and actuator bodies. Preferably the solution should have one or more of the following characteristics: 1) be safer and more reliable than existing methods; 2) allow for simpler, i.e. more economic, manufacture of the inhaler; 3) be easier for the patient to use, especially for children or visually impaired patients; 4) it should produce less detectable extractable and leachable substances than prior art methods in required tests for extractable and leachable substances performed for regulatory approval; and 5) be more reliable than those methods described in the art. There is also a need for improved methods of manufacturing devices of this type.

SUMMARY OF THE INVENTION

Accordingly, a first aspect of the present invention provides a metered-dose inhaler comprising: a medicament-containing vessel; an actuator body for receiving the vessel and having a medicament delivery outlet, wherein the vessel is releasably attachable to the actuator body; a dose counter integrated into the actuator body; and a first indicium on the vessel and a second indicium on the actuator body, wherein the first indicium and the second indicium identify the vessel and the actuator body to be part of the same metered-dose inhaler.

The user therefore may ensure that a given vessel remains paired with a given actuator body, and therefore that the dose counter in the actuator body accurately reflects the remaining number of doses of medicament in the vessel to which the actuator body is attached.

A second aspect of the present invention provides a method for manufacturing a metered-dose inhaler comprising the steps of providing a medicament-containing vessel; providing an actuator body for receiving the vessel and having a medicament delivery outlet; releasably attaching the vessel to the actuator body; and subsequently attaching a first indicium to the vessel and a second indicium to the actuator body, wherein the first indicium and the second indicium identify the vessel and the actuator body to be part of the same metered-dose inhaler.

A third aspect of the present invention provides a method for manufacturing a metered-dose inhaler comprising the steps of providing a medicament-containing vessel; providing an actuator body for receiving the vessel and having a medicament delivery outlet; attaching a first indicium to either the vessel or the actuator body; releasably attaching the vessel to the actuator body; and subsequently attaching a second indicium to whichever of the actuator body and the vessel does not comprise the first indicium, wherein the first indicium and the second indicium identify the vessel and the actuator body to be part of the same metered-dose inhaler.

A fourth aspect of the present invention provides a method for manufacturing a metered-dose inhaler comprising the steps of providing a medicament-containing vessel; attaching a first indicium to the vessel; providing an actuator body for receiving the vessel and having a medicament delivery outlet; attaching a second indicium to the actuator body; and subsequently releasably attaching the vessel to the actuator, wherein the first indicium and the second indicium identify the vessel and the actuator body to be part of the same metered-dose inhaler.

BRIEF DESCRIPTION OF THE DRAWING FIGURES

Figure 2:
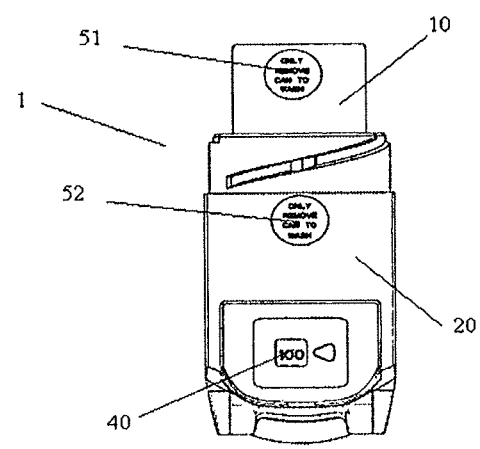

The present invention will now be described with reference to the accompanying drawings, in which:

FIG. 1 and FIG. 2 both show a metered-dose inhaler 1 according to the present invention.

DETAILED DESCRIPTION OF THE INVENTION

The metered-dose inhaler comprises a medicament-containing vessel 10. The vessel 10 may be a pressurised canister containing a mixture of active medicament and propellant. Such canisters may be formed from a deep drawn aluminium cup portion having a crimped lid portion which carries a metering valve assembly or by other methods known to the person skilled in the art as suitable for the manufacture of such canisters. The metering valve assembly is provided with a protruding valve stem which, in use, is inserted as a tight push fit into a so-called "stem block" in the actuator body 20 (see EP 0 966 309).

To actuate the conventional manually-operable inhaler, the user applies a compressive force to the closed end of the canister. The internal components of the metering valve assembly are spring loaded so that, typically, a compressive force of between 15 and 30 N is required to activate the inhaler.

In response to this compressive force, the canister moves axially with respect to the valve stem by an amount varying between about 2 and 4 mm. This degree of axial movement is sufficient to actuate the metering valve and cause a metered quantity of the medicament and propellant to be expelled through the valve stem. This is then released into the medicament delivery outlet 30 via a nozzle in the stem block.

A user inhaling through the medicament delivery outlet 30 of the inhaler at this point will receive a dose of the medicament.

In addition, recently breath-operated actuators have been developed which deliver a dose of medicament through the medicament delivery outlet 30 in response to inhalation by the user. This type of arrangement is particularly convenient in circumstances where the co-ordination between user inhalation and manual depression of the aerosol canister is imperfect. For example, children or the aged sometimes lack the necessary co-ordination to achieve effective self-administration and at times of respiratory distress, adult users may also experience poor co-ordination.

The medicament contained in vessel 10 may be any medicament, or combination of medicaments, that is (are) suitable to be delivered to a patient via a metered-dose inhaler. In particular medicaments for the treatment of a wide variety of respiratory disorders are delivered in this manner including anti-allergic agents (e.g. cromoglycate, ketotifen and nedocromil), anti-inflammatory steroids (e.g. beclomethasone dipropionate, fluticasone, budesonide, flunisolide, ciclesonide, triamcinolone acetonide and mometasone furoate); bronchodilators such as: $\beta_2$-agonists (e.g. fenoterol, formoterol, pirbuterol, reproterol, salbutamol, salmeterol and terbutaline), non-selective $\beta$-stimulants (e.g. isoprenaline), and xanthine bronchodilators (e.g. theophylline, aminophylline and choline theophyllinate); and anticholinergic agents (e.g. ipratropium bromide, oxitropium bromide and tiotropium).

In an embodiment of the invention the vessel contains a medicament in the form of an aerosol. Alternatively in another embodiment of the invention the vessel contains a medicament in the form of a dry powder.

The vessel 10 is releasably attachable to the actuator body 20. This means that the vessel 10 and the actuator body 20 may be attached to each other, and that the vessel 10 and the actuator body 20 may be released from being attached to each other.

Therefore the vessel 10 and actuator body 20 may be connected, for example when the inhaler is in use (see FIG. 1 and FIG. 2), and in addition the vessel 10 and actuator body 20 may be separated, for example when the actuator is being cleaned.

The metered-dose inhaler additionally comprises a dose counter 40 integrated into the actuator body. The dose counter 40 may take any form which allows the number of doses of medicament remaining in the medicament-containing vessel 10 to be monitored.

In an embodiment the dose counter 40 comprises an actuator; a driver for driving a rotary gear in a step-wise fashion in response to displacement of the actuator, the rotary gear comprising a wheel mounted on a spindle which wheel having a plurality of ratchet teeth around its periphery; a resilient member to prevent reverse rotation of the rotary gear; and a display coupled to the rotary gear, the display having a visible array of incrementing integers on a surface thereof indexable by a single integer in response to each step of the step-wise rotary motion of the rotary gear.

The metered-dose inhaler additionally comprises a first indicium 51 on the vessel 10 and a second indicium 52 on the actuator body 20 wherein the first indicium and the second indicium identify the vessel 10 and the actuator body 20 to be part of the same metered-dose inhaler 1.

The vessel 10 and actuator body 20 form part of the same metered-dose inhaler 1 when a dose of medicament from that vessel 10 is delivered only when that vessel 10 is attached to that actuator body 20, and not when it is attached to any other actuator body 20; this allows the dose counter integrated in that actuator body 20 to reflect accurately the number of doses of medicament in that vessel 10.

The crucial role of the indicia is to identify that a particular vessel 10 and actuator body 20 comprise part of the same metered-dose inhaler 1, and consequently that the dose counter 40 integrated into the actuator body 20 accurately reflects the number of doses remaining in the vessel 10.

In an embodiment of the invention the first indicium is attached to the vessel 10 and the second indicium is attached to the actuator body 20.

The indicia may identify the vessel 10 and the actuator body 20 to be part of the same metered-dose inhaler 1 in a variety of different ways. Therefore there must be a link between the first indicium 51 and the second indicium 52 such that the user would make an association between them, and therefore identify that the vessel 10 and actuator body 20 to which they are attached form part of the same metered-dose inhaler 1.

For example, in an embodiment of the metered-dose inhaler 1 the first indicium 51 and the second indicium 52 are substantially the same colour.

In an embodiment of the metered-dose inhaler 1 the first indicium 51 and the second indicium 52 are substantially the same shape.

Preferably the user of the inhaler would make a connection between the first indicium 51 and the second indicium 52 because the first indicium 51 and the second indicium 52 are substantially identical. By substantially identical is meant that that the indicia are very similar or the same, so that a connection between the two is made.

In an embodiment of the invention, the first indicium 51 is a first sticker and the second indicium 52 is a second sticker.

The term sticker is intended to have its usual meaning, namely a substantially planar substrate with an adhesive backing. The adhesive backing must be such that the substrate may be securely attached to the vessel 10 or the actuator body 20.

In an embodiment of the metered-dose inhaler 1 the first sticker is comprises a first insignia and the second sticker comprises a second insignia, such that a user of the inhaler would make a connection between the first insignia and the second insignia. Examples of insignia include, for example, identifying marks, signs, symbols, pictures or characters.

In an embodiment of the metered-dose inhaler 1 the first insignia and the second insignia are substantially identical. By substantially identical is meant that that the insignia are very similar or the same so that a connection between the two insignia is made.

In an embodiment of the metered-dose inhaler 1 the first sticker 51 and the second sticker 52 are substantially identical. By substantially identical is meant that that the stickers are very similar or the same so that a connection between the two stickers is made.

In an embodiment of the invention the first indicium 51 and/or the second indicium 52 are printed, preferably laser printed.

The term printed has its usual meaning of an impression produced in ink.

In an embodiment of the invention the first indicium 51 and/or the second indicium 52 are laser markings.

The term laser marking has its usual meaning of an impression produced by a laser on the surface of a material. Laser marking can be introduced at any point in the manufacturing process after the molding and/or forming of the device parts. Preferably, both the vessel 10 and the actuator body 20 may be laser marked either before, during or after the vessel 10 is releasably attached to the actuator body 20. Typically, best results are obtained by using a polymer resin formulation specially developed for laser marking; however, laser marking may also be used to treat polymeric, metallic, ceramic surface or composite surfaces, e.g. paper.

Laser marking provides a number of advantages over other methods for attaching indicium to either the vessel 10 or the actuator body 20. Firstly, in comparison to other means for attaching indicium it produces an impression with much lower levels of extractable and leachable substances, as detected using the currently required tests for regulatory bodies, e.g. the FDA in the USA, the MI-IRA in the UK, the EMEA in Europe. This is clearly beneficial from a regulatory approval and safety standpoint. In particular, laser marking does not use additional chemicals, such as solvents or corrosive agents (as is the case in other methods such as printing or etching) and has a high permanence of marking.

Other advantages of laser marking include its higher speed, greater precision, increased durability, enhanced sharpness, indelibleness and its ability to mark curved or complex geometry surfaces in comparison with other known methods. It also reduces stock-holding volumes and the risk of product reaching its expiry date before sale.

A further advantage of laser marking is the ability to make quick design changes via the use of computer technology. This is particularly advantageous for its use in the present invention where in some embodiments the first indicium and the second indicium are matched to one another.

An example of lasers suitable for marking the vessel 10 and/or actuator body 20 of the present invention are the Haas VMC2 and VMC4 integrated on a Sortimat Jetwing platform.

Preferably the first indicium 51 and the second indicium 52 are visible when the inhaler is assembled—that is when the vessel 10 is attached to the body 20 so that medicament can be dispensed through the medicament delivery outlet 30.

In addition the metered-dose inhaler 1 may be supplied as a kit. The kit provides the parts such that the user may assemble the metered-dose inhaler 1 according to the invention, and the instructions which detail to the used how to assemble the metered-dose inhaler 1 from those parts.

The kit must therefore provide at least medicament-containing vessel 10, an actuator body 20 with an integrated dose counter 40, a first sticker 51 and a second sticker 52.

In one embodiment the kit comprises: a medicament-containing vessel 10; an actuator body 20 for receiving the vessel 10 and having a medicament delivery outlet; a dose counter 40 integrated into the actuator body 10; and at least one pair of stickers releasably attached to a backing sheet and comprising a first sticker 51 and the second sticker 52 which can be identified as being part of the pair.

The medicament-containing vessel 10, actuator body 20 and dose counter 40 are as described hereinabove.

The first sticker 51 and second sticker 52 are supplied separately to the medicament-containing vessel 10 and actuator body 20. The first sticker 51 and second sticker 52 must be provided in a form suitable to be applied to the vessel 10 and actuator body 20 by the user. For example, the first sticker 51 and the second sticker 52 may be releasably attached to a backing sheet. By releasably attached to a backing sheet is meant that the stickers may be easily removed from the backing sheet by the user, and after removal from the backing sheet may be attached to the vessel 10 and actuator body 20. Such backing sheets are commercially available.

Preferably the kit comprises a plurality of pairs of stickers, wherein each pair of stickers can be distinguished from each other pair. This allows the user of the metered-dose inhaler 1 to select a pair of stickers which are suitable to distinguish the vessel 10 and actuator body 20 of that kit from the vessel 10 and the actuator body 20 of a different kit.

Each pair of stickers must be unambiguously identifiable as being part of that, and only that, particular pair of stickers. Therefore the user would not be confused between a kit comprising a vessel 10 and actuator body 20 which is identified by a particular pair of stickers and a kit comprising a vessel 10 and actuator body 20 which is identified by a another particular pair of stickers. This is particularly important when the user is in possession of more than one inhaler.

Each pair of stickers may be distinguished from each other pair of stickers in a variety of different ways.

In an embodiment of the kit at least one pair of stickers comprises a first sticker and a second sticker which can be identified as being part of that pair by the first sticker 51 and the second sticker 52 being substantially the same colour.

In an embodiment of the kit at least one pair of stickers comprises a first sticker 51 and a second sticker 52 which can be identified as being part of that pair by the first sticker 51 and the second sticker 52 being substantially the same shape.

In an embodiment of the kit at least one pair of stickers comprises a first sticker 51 and a second sticker 52 which can be identified as being part of that pair by the first sticker 51 being illustrated with a first insignia and the second sticker 52 being illustrated with a second insignia, wherein a user of the inhaler would make a connection between the first insignia and the second insignia. Preferably the first sticker and the second sticker can be identified as being part of that pair because the first insignia and the second insignia are substantially identical.

In an embodiment of the kit at least one pair of stickers comprises a first sticker 51 and a second sticker 52 which are substantially identical.

The kit may additionally contain directions to instruct the user as to how to use the stickers in order to distinguish between the medicament-containing vessel 10 and actuator body 20 of that particular kit and those of other kits.

In an embodiment of the kit, the kit additionally comprises instructions to assemble the medicament containing vessel 10 and the actuator body 20 having a medicament delivery outlet 30 to form a metered-dose inhaler 1, and use one pair of stickers by attaching the first sticker 51 of the pair to the vessel 10 and the second sticker 52 of the pair to the actuator body 20 to identify the vessel 10 and the actuator body 20 to be part of the same metered-dose inhaler 1.

The present invention also encompasses methods for manufacturing metered-dose inhalers.

A first method for manufacturing a metered-dose inhaler comprises the steps of providing a medicament-containing vessel 10; providing an actuator body 20 for receiving the vessel 10 and having a medicament delivery outlet; releasably attaching the vessel 10 to the actuator body 20; and subsequently attaching a first indicium 51 to the vessel 10 and a second indicium 52 to the actuator body 20, wherein the first indicium 51 and the second indicium 52 identify the vessel 10 and the actuator body 20 to be part of the same metered-dose inhaler.

This method has the advantage of removing the need to match vessels to corresponding actuator bodies because the indicium 51, 52 are only attached to the actuator body 20 and the vessel 10 once the vessel 10 has been releasably attached to the actuator body 20.

A second method for manufacturing a metered-dose inhaler comprises the steps of providing a medicament-containing vessel 10; providing an actuator body 20 for receiving the vessel 10 and having a medicament delivery outlet; attaching a first indicium 51 to either the vessel 10 or the actuator body 20; releasably attaching the vessel 10 to the actuator body 20; and subsequently attaching a second indicium 52 to whichever of the actuator body 20 and the vessel 10 does not comprise the first indicium 51, wherein the first indicium 51 and the second indicium 52 identify the vessel 10 and the actuator body 20 to be part of the same metered-dose inhaler.

A third method for manufacturing a metered-dose inhaler comprises the steps of providing a medicament-containing vessel 10; attaching a first indicium 51 to the vessel 10; providing an actuator body 20 for receiving the vessel 10 and having a medicament delivery outlet; attaching a second indicium 52 to the actuator body 20; and subsequently releasably attaching the vessel 10 to the actuator 20, wherein the first indicium 51 and the second indicium 52 identify the vessel 10 and the actuator body 20 to be part of the same metered-dose inhaler.

The above methods all have advantages in terms of simplicity of manufacture, reproducibility and speed.

In preferred embodiments of the above methods, at least one of the first indicium 51 and the second indicium 52 is a sticker, preferably the first indicium 51 is a sticker and the second indicium 52 is a sticker.

In further preferred embodiments of the methods, at least one of the first indicium 51 and the second indicium 52 comprises a laser marking, preferably the first indicium 51 comprises a laser marking and the second indicium 52 comprises a laser marking.

In still further embodiments of the methods at least one of the first indicium 51 and the second indicium 52 is printed.

In an embodiment of the methods the first indicium 51 and the second indicium 52 are substantially identical.

In an embodiment the first indicium 51 and the second indicium 52 comprise symbols, pictures, numbers and/or letters.

In a particular preferred embodiment of the invention the vessel 10 and/or the actuator body 20 comprise a manufacturing batch number and the first indicium 51 and the second indicium 52 comprise the manufacturing batch number of either the vessel 10 or the actuator body 20, preferably the manufacturing batch number of the vessel 10. The manufacturing batch number has it usual meaning of an identification comprising a series of numbers and/or letters which identify parts, in this case vessels 10 or actuator bodies 20, as having been made in the same batch of a batch manufacturing process.

This embodiment has the advantage of minimising the number of total manufacturing steps. It is a regulatory requirement to have batch numbers for both the vessel 10 and the actuator body 20 to enable traceability. By copying either the batch number assigned to the vessel 10 onto the actuator body or the batch number of the actuator body 20 onto the vessel 10, there is no need to generate a new indicium for preventing mismatching and attach the generated new indicium to vessel 10 and to the actuator body 20. Typically, a batch will comprise at least two parts, typically between 2 and 1,000,000 parts, even more typically between 100,000 and 500,000, most typically 400,000.

Although the invention herein has been described with reference to particular embodiments, it is to be understood that these embodiments are merely illustrative of the principles and applications of the present invention. It is therefore to be understood that numerous modifications may be made to the illustrative embodiments and that other arrangements may be devised without departing from the spirit and scope of the present invention as defined by the appended claims.

What is claimed is:

1. A method for allowing a user of a metered dose inhaler to distinguish a vessel and actuator body of a kit from the vessel and actuator body of a different kit comprising the steps of:
    providing a plurality of individual kits, each individual kit comprising:
        a single medicament-containing vessel;
        a single actuator body for receiving the vessel and having a medicament delivery outlet;
        a dose counter integrated into the actuator body; and
        a plurality of pairs of stickers for each individual kit, the plurality of pairs of stickers releasably attached to a backing sheet, each pair of the plurality of pairs of stickers comprising a first sticker and a second sticker which can be identified as being part of the pair, wherein each pair of the plurality of pairs of stickers can be distinguished from each other pair of the plurality of pairs of stickers; and
    directing the user to subsequently select a pair of stickers from the plurality of pairs of stickers and then remove the selected pair of stickers from the backing sheet and apply the selected pair of stickers to the medicament-containing vessel and actuator body of one of the individual kits selected from the plurality of individual kits; wherein the selected pair of stickers distinguishes the vessel and actuator body of the selected individual kit from the vessel and actuator body of a different individual kit of the plurality of individual kits; and wherein each medicament-containing vessel of the plurality of individual kits contains the same medicament.

2. The method of claim 1, wherein at least one pair of stickers comprises a first sticker and a second sticker which can be identified as being part of the at least one pair by the first sticker and the second sticker being substantially the same color.

3. The method of claim 1, wherein at least one pair of stickers comprises a first sticker and a second sticker which can be identified as being part of the at least one pair by the first sticker and the second sticker being substantially the same shape.

4. The method of claim 1, wherein at least one pair of stickers comprises a first sticker and a second sticker which can be identified as being part of the at least one pair by the first sticker comprising a first insignia and the second sticker comprising a second insignia such that a user of the inhaler would make a connection between the first insignia and the second insignia.

5. The method of claim 4, wherein the first insignia and the second insignia are substantially identical.

6. The method of claim 1, wherein at least one pair of stickers comprises a first sticker and a second sticker which can be identified as being part of the at least one pair by the first sticker and the second sticker being substantially identical.

7. The method of claim 1, wherein each individual kit additionally comprises instructions to assemble the medicament containing vessel and the actuator body having a medicament delivery outlet to form a metered-dose inhaler, and use one pair of stickers by attaching the first sticker of the pair to the vessel and the second sticker of the pair to the actuator body to identify the vessel and the actuator body to be part of the same metered-dose inhaler.

8. The method of claim 1, wherein at least one pair of stickers of one of the plurality of individual kits differs from at least one pair of stickers of another of the plurality of individual kits.

9. The method of claim 1, wherein a sticker of the plurality of pairs of stickers is configured to be positioned on the actuator body such that it is radially aligned with the dose counter.

10. The method of claim 1, wherein the pairs of stickers of one of the plurality of individual kits differs from the pairs of stickers of another of the plurality of individual kits.

11. The method of claim 1, wherein each individual kit further comprises directions to instruct a user as to how to use the pairs of stickers in order to distinguish between the medicament containing vessel and the actuator body of one of the plurality of individual kits from the medicament containing vessel and the actuator body of another of the plurality of individual kits.

* * * * *